United States Patent
Nickisch et al.

(10) Patent No.: US 11,195,278 B2
(45) Date of Patent: Dec. 7, 2021

(54) FRACTIONAL FLOW RESERVE SIMULATION PARAMETER CUSTOMIZATION, CALIBRATION AND/OR TRAINING

(71) Applicant: KONINKLIJKE PHILIPS N.V., Eindhoven (NL)

(72) Inventors: Hannes Nickisch, Hamburg (DE); Holger Schmitt, Luetjensee (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 130 days.

(21) Appl. No.: 16/500,245

(22) PCT Filed: Apr. 6, 2018

(86) PCT No.: PCT/EP2018/058885
§ 371 (c)(1),
(2) Date: Oct. 2, 2019

(87) PCT Pub. No.: WO2018/185298
PCT Pub. Date: Oct. 11, 2018

(65) Prior Publication Data
US 2021/0110543 A1   Apr. 15, 2021

Related U.S. Application Data

(60) Provisional application No. 62/482,231, filed on Apr. 6, 2017, provisional application No. 62/535,264, filed on Jul. 21, 2017.

(51) Int. Cl.
*G16H 50/50* (2018.01)
*G16H 10/60* (2018.01)
(Continued)

(52) U.S. Cl.
CPC .......... *G06T 7/0014* (2013.01); *A61B 5/0044* (2013.01); *A61B 5/14535* (2013.01);
(Continued)

(58) Field of Classification Search
None
See application file for complete search history.

(56) References Cited

U.S. PATENT DOCUMENTS

9,167,974 B2 * 10/2015 Taylor .................. G06K 9/6298
10,052,158 B2 * 8/2018 Taylor ..................... A61B 6/504
(Continued)

FOREIGN PATENT DOCUMENTS

WO   WO2016087396 A1   6/2016

OTHER PUBLICATIONS

PCT International Search Report, International application No. PCT/EP2018/058885, dated Jul. 10, 2018.
(Continued)

*Primary Examiner* — Idowu O Osifade
(74) *Attorney, Agent, or Firm* — Larry Liberchuk

(57) ABSTRACT

A computing system (118) includes a computer readable storage medium (122) with computer executable instructions (124), including a including a biophysical simulator (126) with a segmentor (202) and a boundary condition determiner (206). The computing system further includes a processor (120) configured to execute the biophysical simulator to compute a fractional flow reserve index with cardiac imaging data and at least one of an adapted coronary tree segmentation and an adapted boundary condition.

23 Claims, 4 Drawing Sheets

(51) Int. Cl.

| | |
|---|---|
| *A61B 5/00* | (2006.01) |
| *A61B 5/145* | (2006.01) |
| *G06T 7/00* | (2017.01) |
| *G06T 7/10* | (2017.01) |
| *G16H 50/30* | (2018.01) |

(52) U.S. Cl.
CPC .............. *A61B 5/7475* (2013.01); *G06T 7/10* (2017.01); *G16H 10/60* (2018.01); *G16H 50/30* (2018.01); *G16H 50/50* (2018.01); *G06T 2207/20081* (2013.01); *G06T 2207/30048* (2013.01)

(56) References Cited

U.S. PATENT DOCUMENTS

| | | | |
|---|---|---|---|
| 10,258,303 | B2 | 4/2019 | Grass |
| 10,622,110 | B2* | 4/2020 | Itu .......................... A61B 6/481 |
| 2014/0236547 | A1 | 8/2014 | Itu |
| 2015/0092999 | A1 | 4/2015 | Schmitt |
| 2015/0112191 | A1 | 4/2015 | Gilboa |
| 2015/0269351 | A1 | 9/2015 | Taylor |
| 2015/0282765 | A1 | 10/2015 | Goshen |
| 2016/0133015 | A1* | 5/2016 | Taylor ................... A61B 5/0044 382/128 |
| 2016/0148372 | A1 | 5/2016 | Itu |
| 2016/0300349 | A1* | 10/2016 | Fonte ..................... A61B 5/026 |
| 2017/0017771 | A1 | 1/2017 | Koo |
| 2017/0105694 | A1 | 4/2017 | Grass |
| 2017/0329930 | A1* | 11/2017 | Fonte ................. A61B 5/02007 |
| 2020/0126672 | A1* | 4/2020 | Rabbat ................... G16H 50/30 |
| 2021/0074435 | A1* | 3/2021 | Taylor ................... G16H 10/60 |

OTHER PUBLICATIONS

Tu Shengxian et al., "Fractional Flow Reserve Calculation From 3-Dimensional Quantitative Coronary Angiography and TIMI Frame Count A Fast Computer Model to Quantify the Functional Significance of Moderately Obstructed Coronary Arteries", JACC: Cardiovascular Interventions, Elsevier, Amsterdam, NL, vol. 7, No. 7, Jul. 21, 2014 (Jul. 21, 2014), pp. 768-777.

Gargiulo G. et al., "Diabetes Does Not Impact the Diagnostic Performance of Conlrast-Based Fractional Flow Reserve: Insights from the CONTRAST Study", Cardiovascular Diabetology, vol. 16, No. 1, Jan. 13, 2017 (Jan. 13, 2017).

Mehta S.M. et al., "Association of Lower Fractional Flow Reserve Values With Higher Risk of Adverse Cardiac Events for Lesions Deferred Revascularization Among Patients With Acute Coronary Syndrome", Journal of the American Heart Association, vol. 4, No. 8, Aug. 19, 2015 (Aug. 19, 2015), p. e002172, XP055487317.

Lemic A. et al., "Semi-Automatic Segmentation of Coronary Arteries in CT Images", Jun. 6, 2016 (Jun. 6, 2016), XP055487267,Retrieved from the Internet: URL:http://lup.lub.lu.se/student-papers/re cord/8879728/file/8879735.pdf, [retrieved on Jun. 22, 2018].

Nickisch H. et al.,"Learning Patient-Specific Lumped Models for Interactive Coronary Blood Flow Simulations", Medical Image Computing and Computer-Assisted Intervention—MICCAI 2015: 18th International Conference, LNCS, vol. 9350, pp. 433-441, 2015.

Freiman M. et al., "Improving CCTA-Based Lesions' Hemodynamic Significance Assessment by Accounting for Partial Volume Modeling in Automatic Coronary Lumen Segmentation", Medical Physics, vol. 44, issue 3, pp. 1040-1049, 2017.

Zheng Y. et al., "Robust and Accurate Coronary Artery Centerline Extraction in CTA by Combining Model-Driven and Data-Driven Approaches," Med Image Comput Assist Interv. 2013;16(Pt 3):74-81.

Ecabert O. et al., "Segmentation of the Heart and Great Vessels in CT Images Using a Model-Based Adaptation Framework," Medical Image Analysis, vol. 15, issue 6, Dec. 2011, pp. 863-876.

* cited by examiner

| Hydraulic Effect | Geometry weights $w_e$, coefficients $\alpha_e$ and degrees $d_e$ | | Pictogram |
|---|---|---|---|
| 1) Poiseuille friction | $w_P = 8\pi\mu \frac{\ell}{A^2}$ | $d_P = 1$ | |
| 2) Expansion friction [18] | $w_E = \frac{\rho}{2}\max^2(0, \frac{1}{A_P} - \frac{1}{A_{next}})$ | $d_E = 2$ | |
| 3) Ovality friction [11] | $w_O = w_P \cdot \left(\frac{P^2}{4\pi A}\right)^{\frac{1}{2}}$ | $d_O = 1$ | |
| 4) Curvature friction [1] | $w_C = w_P \cdot \max\left(0, \frac{10}{7}(r\kappa)^{\frac{1}{2\pi}} - 1\right)$ | $d_C = 1$ | |
| 5) Bernoulli's principle | $w_B = \frac{\rho}{2}(\frac{1}{A^2} - \frac{1}{A_{next}^2})$ | $d_B = 2$ | |
| 6) Bifurcation friction [19] | $w_{B_0} = \frac{\rho}{2A_P^2}$, $w_{B_1} = \frac{\rho}{2A_{out,1}^2}$, $w_{B_2} = \frac{\rho}{2A_{out,2}^2}$ | $d_{B_0} = d_{B_1} = d_{B_2} = 2$ | |

FIGURE 8

FRACTIONAL FLOW RESERVE SIMULATION PARAMETER CUSTOMIZATION, CALIBRATION AND/OR TRAINING

FIELD OF THE INVENTION

The following generally relates to imaging and more particularly to fractional flow reserve simulation (FFR) customization, calibration and/or training, and is described with particular application to FFR—computed tomography (FFR-CT), and is also amenable to x-ray FFR.

BACKGROUND OF THE INVENTION

Fractional flow reserve (FFR) is an invasive measure in the catheterization laboratory (Cath Lab) to quantify, via an FFR index, the hemodynamic significance of a coronary lesion due to calcified or soft plaque. The index indicates the functional severity of a coronary stenosis that is calculated from pressure measurements made during coronary arteriography and is defined as the distal blood pressure (behind a stenosis) relative to the proximal pressure (close to the ostium) under hyperemic conditions. That is, the FFR index expresses the maximal flow down a vessel in the presence of a stenosis compared to the maximal flow in the hypothetical absence of the stenosis. The FFR value is an absolute number between 0 and 1, where a value 0.50 indicates that a given stenosis causes a 50% drop in blood pressure.

An invasive FFR procedure requires insertion of a catheter into the femoral or radial arteries and advancement of the catheter to the stenosis where a sensor at the tip of the catheter senses pressure across the stenosis, during conditions promoted by various agents that effect vessel geometry, compliance and resistance, and/or other characteristics. A non-invasive approach estimates an FFR index from CT image data of the heart (e.g., from contrast enhanced coronary computed tomography angiography, CCTA) through computational fluid dynamic (CFD) simulations in which blood flow and pressure through the coronaries are simulated. This includes using CCTA image data to derive a geometrical model of the coronary tree, extract features therefrom, and determine boundary conditions from the features for the simulation.

FFR-CT simulation software has been deployed at a clinical site with pre-set, factory-tuned algorithm parameters, e.g., for segmentation of the coronaries from the CCTA image, or scaling factors for peripheral resistances which control the simulated flow of blood through the coronaries. However, usage patterns, individual habits, and/ or patient populations may vary from site to site. For example, when segmenting a vessel, one clinician may segment inside an inside surface of a vessel wall, while another clinician segments on the vessel wall. In another example, the actual perimeter of the vessel wall may be clearer in a higher image quality image relative to a lower the image quality image. As a result, an accuracy of FFR-CT simulation results may vary from clinician to clinician, site to site, etc.

SUMMARY OF THE INVENTION

Aspects described herein address the above-referenced problems and others.

In one aspect, a computing system includes a computer readable storage medium with computer executable instructions, including a biophysical simulator with a segmentor and a boundary condition determiner. The computing system further includes a processor configured to execute the biophysical simulator to compute a fractional flow reserve index with cardiac imaging data and at least one of an adapted coronary tree segmentation and an adapted boundary condition.

In another aspect, a computer readable storage medium is encoded with computer readable instructions, which, when executed by a processor of a computing system, causes the processor to: receive cardiac imaging data, and execute a biophysical simulator to compute a fractional flow reserve index with the cardiac imaging data and at least one of an adapted coronary tree segmentation and an adapted boundary condition.

In another aspect, a method includes receiving cardiac imaging data, and computing a fractional flow reserve index with the cardiac imaging data and at least one of an adapted coronary tree segmentation and an adapted boundary condition.

Those skilled in the art will recognize still other aspects of the present application upon reading and understanding the attached description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

FIG. 8 illustrates a table reflecting vessel geometry and hydraulic effects.

DETAILED DESCRIPTION OF EMBODIMENTS

Figure 1:
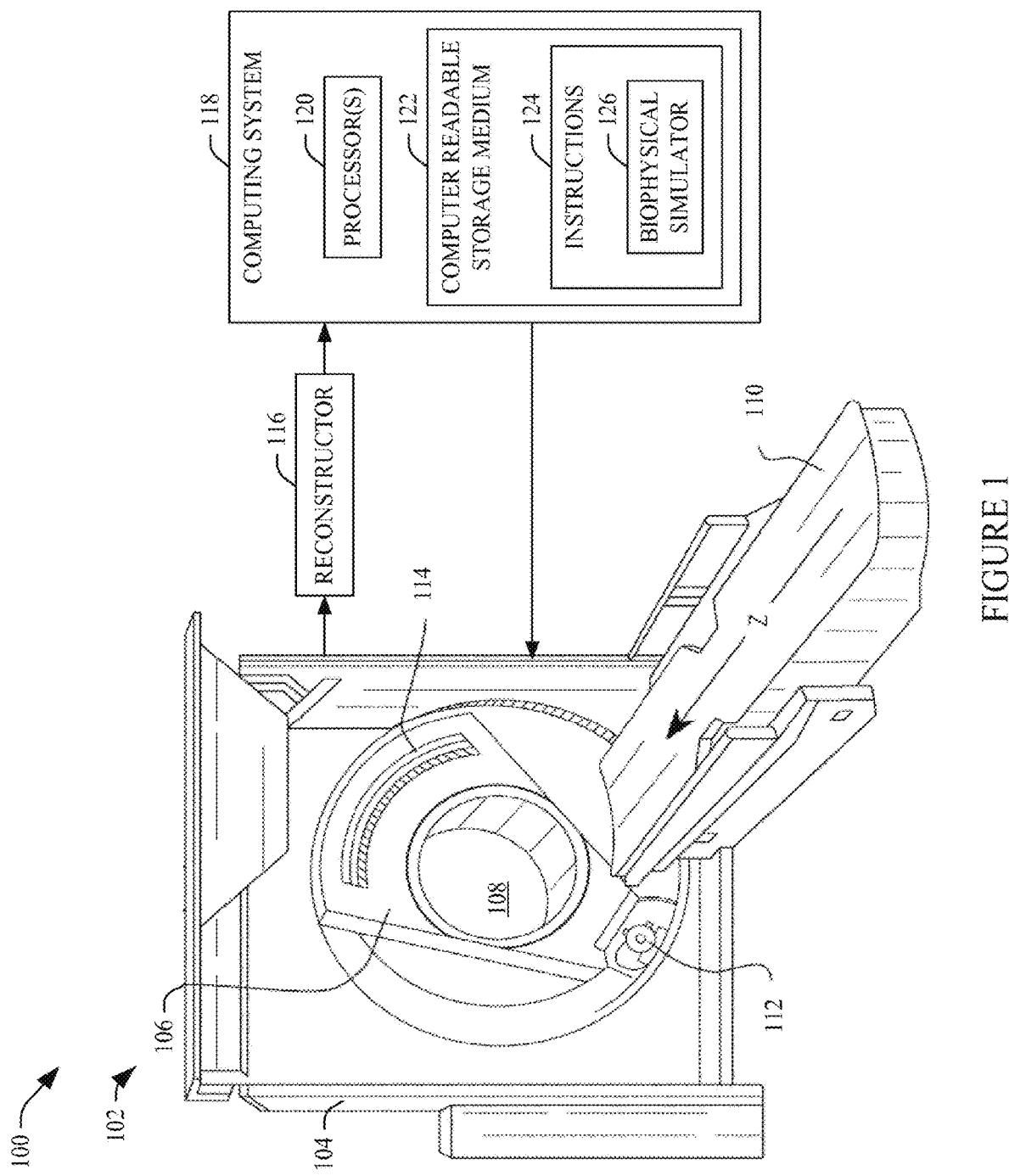
FIG. 1 schematically illustrates a system, including a computing system and an imaging system.

FIG. 1 schematically illustrates a system 100 including an imaging system 102 such as a CT scanner. In a variation, the system 100 includes an x-ray imager. The imaging system 102 includes a generally stationary gantry 104 and a rotating gantry 106, which is rotatably supported by the stationary gantry 104 and rotates around an examination region 108 about a z-axis. A subject support 110, such as a couch, supports an object or subject in the examination region 108.

A radiation source 112, such as an x-ray tube, is rotatably supported by the rotating gantry 106, rotates with the rotating gantry 106, and emits radiation that traverses the examination region 108. A radiation sensitive detector array 114 subtends an angular arc opposite the radiation source 112 across the examination region 108B. The radiation sensitive detector array 114 detects radiation traversing the examination region 108 and generates an electrical signal(s) (projection data) indicative thereof. A reconstructor 116 reconstructs the projection data, generating volumetric image data indicative of a scanned portion of a subject or object located in the examination region 108.

A computing system 118, in this example, serves as an operator console. The console 118 includes a processor 120 (e.g., a microprocessor, a central processing unit, etc.) and a computer readable storage medium 122, which excludes transitory medium, and includes non-transitory medium such as a physical memory device, etc. The console 118 further includes a human readable output device(s) such as a monitor, and an input device(s) such as a keyboard, mouse, etc.

The computer readable storage medium 122 includes instructions 124 for at least a biophysical simulator 126. The processor 120 is configured to execute the instructions 124 and/or software that allows the operator to interact with and/or operate the scanner 102 via a graphical user interface (GUI) or otherwise. The processor 120 may additionally, or alternatively, execute a computer readable instruction(s) carried by a carrier wave, a signal and/or other transitory medium.

In a variation, the biophysical simulator 126 is part of another computing system, which is separate from the console 118 and the system 100. In this instance, the other computing system is similar to the console 118 in that it includes a processor, computer readable storage medium, etc., but it does not include software that allows the operator to interact with and/or operate the scanner 102.

The biophysical simulator 126 is configured to process at least the volumetric image data to perform a biophysical simulation. With respect to FFR, the biophysical simulator determines an FFR index based CCTA image data (or an x-ray angiogram). The FFR index can be displayed via a display monitor, stored, conveyed to another device, etc. As described in greater details below, the biophysical simulator 126 includes one or more feedback loops such as a segmentation feedback loop and/or a boundary condition feedback loop. The feedback loops can be used for training, simulation customization and/or calibration, and/or predictive purposes for individual clinicians, sites, etc.

As such, the biophysical simulator 126 can be deployed at a clinical site and tuned to individual users and/or the site, e.g., for segmentation of the coronary tree from the CCTA image data (or the x-ray angiogram), or scaling factors for peripheral resistances which control the simulated flow of blood through the coronary arteries. In one instance, this mitigates different outcomes for usage patterns, individual habits, and/or patient populations that vary from site to site. As a consequence, an accuracy of FFR-CT (or x-ray FFR) simulation results from clinician to clinician, site to site, etc. may improve relative to a configuration in which the approach described herein is not utilized and/or the biophysical simulator 126 described herein is omitted.

Figure 2:
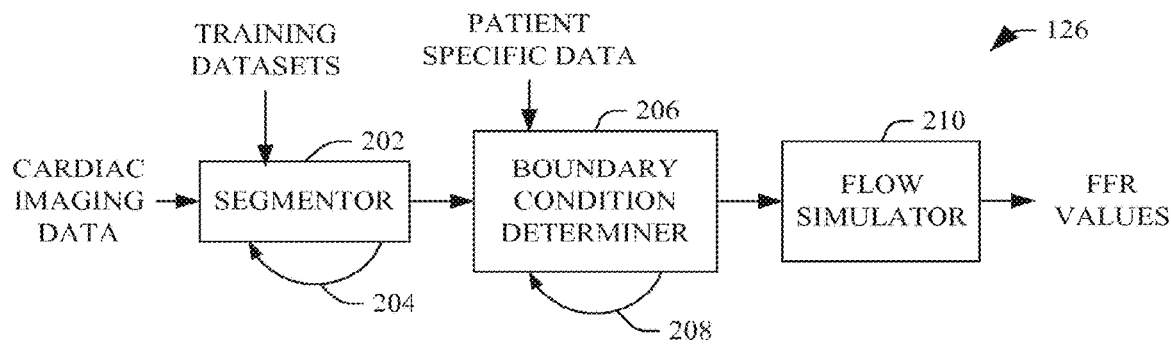
FIG. 2 illustrates an example biophysical simulator.

FIG. 2 schematically illustrates an example of the biophysical simulator 126 in connection with FFR-CT. In this example, the biophysical simulator 126 includes a segmentor 202 with a segmentation feedback loop 204, a boundary condition determiner 206 with a boundary condition feedback loop 208, and a flow simulator 210. In a variation, the segmentation feedback loop 204 is omitted. In another variation, the boundary condition feedback loop 208 is omitted. The biophysical simulator 126 receives, as input, CCTA imaging data from the imaging system 100, a data repository (e.g., a radiology information system (RIS), a picture and archiving system (PACS), etc.), and/or other apparatus.

Figure 3:
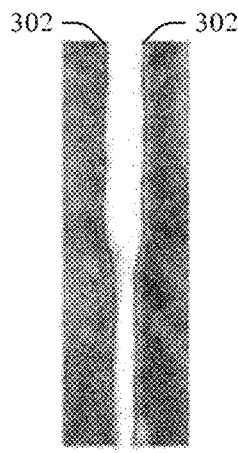
FIG. 3 illustrates an example segmentation of the coronary arteries.
Figure 4:
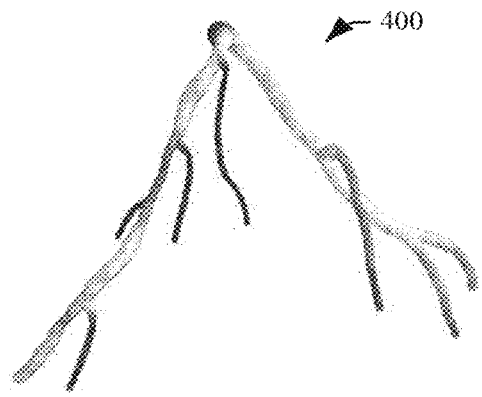
FIG. 4 illustrates an example anatomical model of the coronary arteries.

The segmentor 202 employs a segmentation algorithm to segment the coronary tree from the CCTA imaging data. The segmentation can be performed automatically (e.g., machine learning, etc.) or semi-automatically (e.g., with user assistance). In one instance, the segmentation includes identifying and/or extracting coronary artery centerlines and/or lumen geometry (e.g., diameter, perimeter, cross-sectional area, etc.) therefrom. The segmentation can be based on voxel intensity, object shape, and/or other characteristics. FIG. 3 shows segmentation of a portion of an individual vessel showing opposing walls 302 of the vessel lumen, and FIG. 4 shows a segmented coronary tree 400.

Examples of suitable approaches for extracting a coronary tree from CCTA imaging data are discussed in Zheng et al., "Robust and accurate coronary artery centerline extraction in CTA by combining model-driven and data-driven approaches," Med Image Comput Assist Interv. 2013; 16(Pt 3):74-81, Ecabert et al., "Segmentation of the heart and great vessels in CT images using a model-based adaptation framework," Med Image Anal. 2011 December; 15(6):863-76, and Freiman et al., "Improving CCTA-based lesions' hemodynamic significance assessment by accounting for partial volume modeling in automatic coronary lumen segmentation," Med Phys. 2017 March; 44(3):1040-1049. Other approaches are also contemplated herein.

In one instance, the CCTA imaging data is a training set, and experts have already have performed an accurate coronary tree segmentation that results in simulation of an FFR index that matches known "ground truth" invasive FFR measurements, providing a reference segmentation for the training set. The segmentor 202 segments the coronary tree from the training set, and a user freely manipulates the coronary tree segmentation with the tools of the segmentor 202. The segmentor 202 compares the user adjusted coronary tree segmentation with the reference segmentation. The segmentor 202, via the feedback loop 204, provides feedback indicating any differences between the user adjusted coronary tree segmentation and the reference segmentation. The feedback may indicate whether a subsequent adjusted coronary tree segmentation is closer to the reference segmentation, a recommendation for improving the segmentation, and/or other information about the segmentation.

In another instance, the CCTA imaging data again is the training set. The segmentor 202, in this instance, learns differences between the user adjusted coronary tree segmentation and the reference segmentation and stores the deviations as user-specific calibration data. The segmentor 202 utilizes the user-specific calibration data, e.g., to automatically adapt a subsequent user adjusted coronary tree segmentation from patient CCTA imaging data under evaluation or analysis (a non-training data set). For this, the segmentor 202, via the feedback loop 204, visually presents an adapted adjusted coronary tree segmentation based on the user-specific calibration data. For the adaption, the segmentor 202 may shift one or more points of a segmentation. For example, the segmentor 202 can increase or decrease a diameter of a segmented coronary vessel, move a wall of a segmented coronary vessel, etc.

The user can accept, reject and/or modify the visually presented adapted adjusted coronary tree segmentation. The user may also redo the segmentation. The user may periodically use the training set (and/or another training set) to update their user-specific calibration data. For instance, over time, the user's ability to create an adjusted coronary tree segmentation that is more accurate relative to the reference may increase with experience. In such an instance, the current user-specific calibration data may overcorrect. For this, the user can process the training set (and/or the other training set), and segmentor 202 can update the user-specific calibration data based on the deviations therefrom. Additionally, or alternatively, the segmentor 202, upon start up or otherwise, may present a training set to the user to update their user-specific calibration data.

The boundary condition determiner 206 determines boundary conditions for a computational fluid dynamic simulation of blood flow in vessels from the user adjusted coronary tree segmentation and/or the segmentor 202 adapted user adjusted coronary tree segmentation.

With one approach, a parametric lumped model is employed. The model includes a centerline representation using nonlinear resistances, with elements indicating inflow and outflow boundary conditions, and elements representing tree segment transfer functions, which include a series of linear and nonlinear resistance elements reflecting vessel geometry (e.g., diameter, perimeter, cross-sectional area, etc.) and/or hydraulic effects (e.g., 1-6 in FIG. 8).

FIG. 8. Hydraulic Effects, where A >local cross-sectional area of a vessel, P=a perimeter of the vessel, l=a length of the vessel, r=a radius of the vessel and k=a curvature of the vessel, p=the density of blood, and u=the viscosity of blood.

An example of a lumped model is discussed in Nickisch, et al., "Learning Patient-Specific Lumped Models for Interactive Coronary Blood Flow Simulations," in Medical Image Computing and Computer-Assisted Intervention—MICCAI 2015: 18th International Conference, LNCS, Vol. 9350, 2015, vol. 9350, pp. 433-441. An example of deriving boundary conditions is described in EP14174891.3, filed Jun. 30, 2014, and entitled "Enhanced Patient's Specific Modelling For FFR-CT," which is incorporated herein by reference in its entirety. Other approaches are also contemplated herein.

In the illustrated example, patient-specific data collected after the FFR-CT simulation is provided to the boundary condition determiner 206. Non-limiting examples of such data include, but are not limited to, hematocrit, presence/absence of diabetes, acute coronary syndrome, and blood pressure. The data can be provided by a user, extracted from an electronic patient record, and/or otherwise retrieved. The patient-specific data is used, via the feedback loop 208, to update boundary conditions. For example, invasive FFR measurements for patients who had previously undergone FFR-CT simulation can be used to improve future simulations. Furthermore, documented outcomes, additional biophysical and/or functional measurements may be used to readjust the boundary conditions.

The following provides non-limiting examples of how patient-specific data can be utilized. Hematocrit is a measure of a volume percentage of red blood cells. Generally, an increased hematocrit means a higher value of the viscosity of blood. The viscosity of blood can be adjusted using an empirical curve, e.g., a linear scaling between 40%-45%. The presence of diabetes generally means stiffer walls and higher myocardial resistance. The corresponding resistance boundary condition can be adjusted, e.g., by adding 10% to the default value. Where the cut-off FFR threshold for treatment is 0.80, this threshold can be increased, e.g., to 0.85, for a patient with acute coronary syndrome (ACS), to ensure that borderline patients are treated.

Additional invasive reference FFR measurements for a particular patient can be used to adapt any model parameter e.g. the myocardial resistance so as to obtain a better match between reference and model prediction (given the current segmentation). This can be done by gradient descent, parameter search, etc. Documented patient outcome such as cardiac events or survival data can be used in a similar way to adapt parameters taking the previously obtained model prediction and the medical treatment into account. For example, if a lesion was considered insignificant via a CT-FFR assessment and that lesion caused a major cardiac event, then the assessment can be reconsidered and parameters such as the FFR threshold can be updated to better match the outcome.

Additionally, or alternatively, for one or more input parameters, the boundary condition determiner 206 also determines boundary conditions for one or more predetermined variations in the input parameter. For example, for a measured blood pressure of X, the boundary condition determiner 206 can also determine boundary conditions for at least a blood pressure values of (X)(±0.Z), where Z represents a tolerance as a percentage such as 1%, 2%, 5%, 10%, 25%, etc. This allows the computing system 118 to compute FFR values for the input parameter as well as a value(s) around the input value. The computed FFR values will indicate how the values of a parameter effects the outcome of the FFR-CT simulation.

Where a confidence of a parameter value (e.g., a measured blood pressure) is low, and a small change in the value has a significant effect on the FFR value (e.g., changes the recommendation from observe the patient to treat the patient), the user may choose to acquire and use a more accurate value, rather than use the current value. Alternatively, the user may proceed with the understanding of how this parameter value effects the FFR value. Alternatively, the user may proceed without using this parameter value and/or adjusting boundary conditions affected by this parameter. Where a confidence of a parameter value is high, the user may continue with the value.

The flow simulator 210 performs a flow simulation with the boundary conditions and generates and outputs FFR values. Flow simulations can be done, e.g., using a computational fluid dynamics (CFD) approach and/or other approach. Examples of computing FFR values are described in US 2015/0092999 A1, filed May 10, 2013, and entitled "Determination of a fractional flow reserve (FFR) value for a stenosis of a vessel," US 2015/0282765 A1, filed Oct. 24, 2013, and entitled "Fractional flow reserve (FFR) index," which are incorporated herein by reference in their entireties.

Figure 5:
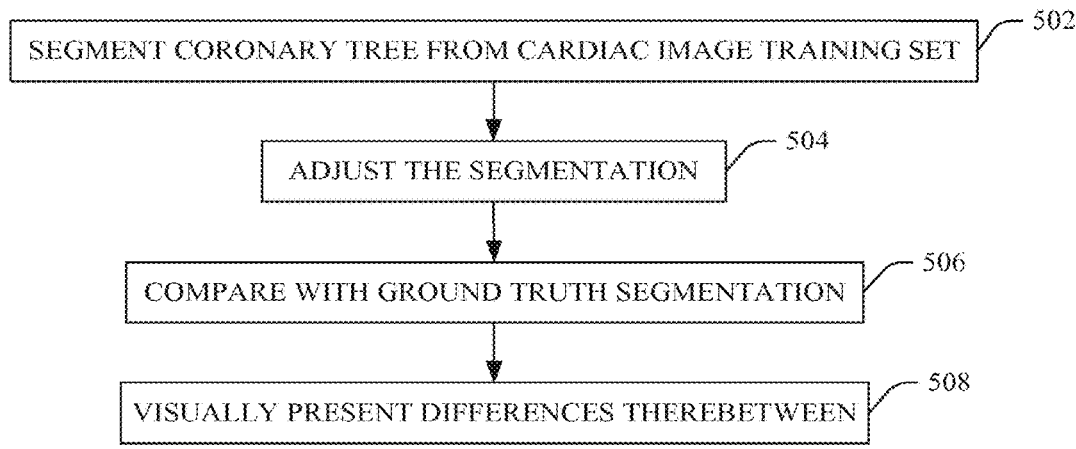
FIG. 5 illustrates an example method in accordance with an embodiment herein.

FIG. 5 illustrates an example method in accordance with an embodiment described herein.

At 502, a coronary vessel is segmented from a training set of CCTA imaging data.

At 504, a user input indicative of an adjustment to the segmentation is received and applied to the segmented vessel, producing a user adjusted coronary vessel segmentation.

At 506, the user adjusted coronary vessel segmentation is compared with a reference vessel segmentation for the training set.

At 508, a difference between the segmentations is visually presented. The difference can be graphical and/or numerical.

This method is well-suited for coronary tree segmentation training.

Figure 6:
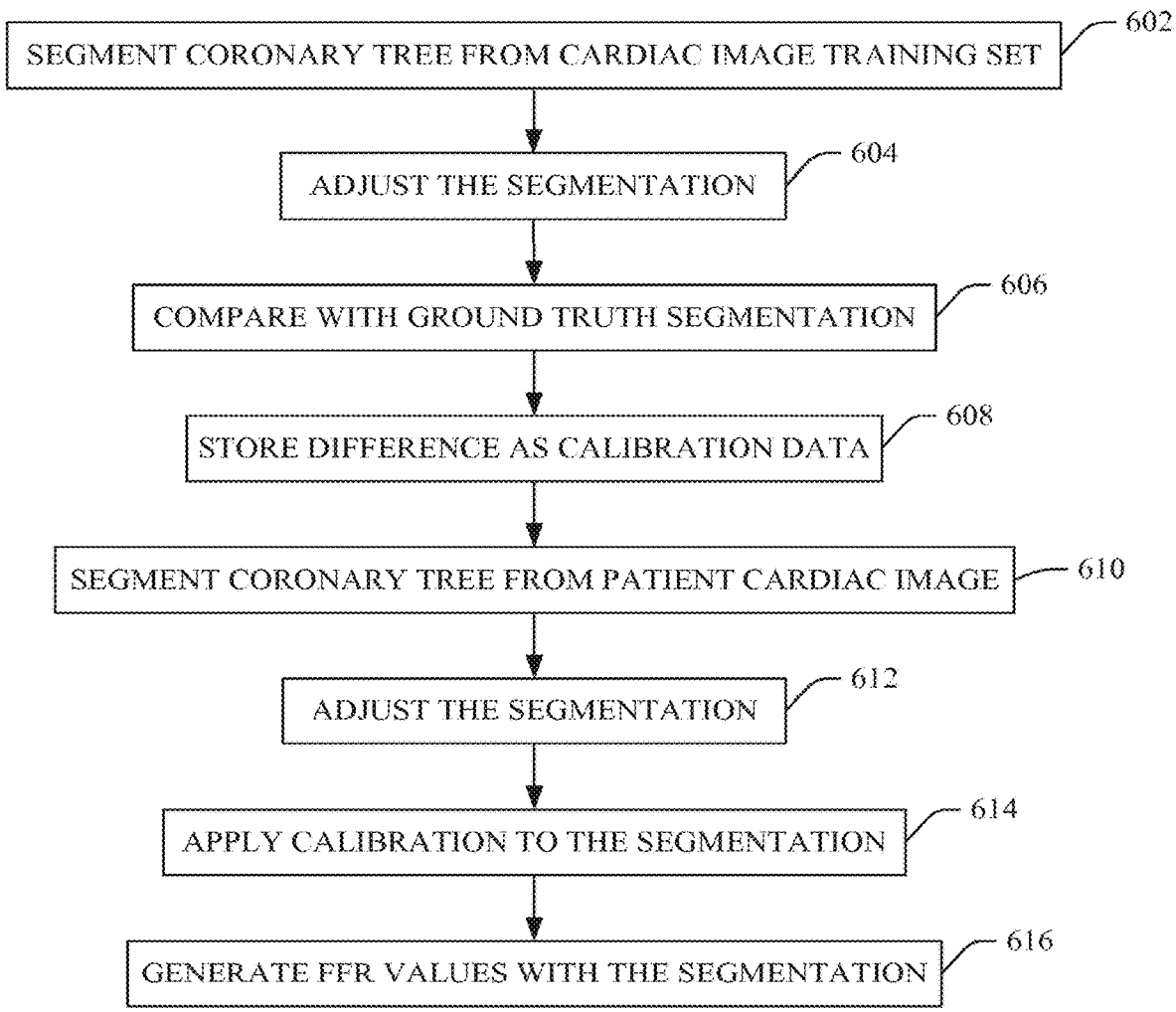
FIG. 6 illustrates another example method in accordance with an embodiment herein.

FIG. 6 illustrates another example method in accordance with an embodiment described herein.

At 602, a coronary tree is segmented from a training set of CCTA imaging data.

At 604, a user input indicative of an adjustment to the segmentation is received and applied to the segmented tree, producing a user adjusted coronary tree segmentation.

At 606, the user adjusted coronary tree segmentation is compared with a reference tree segmentation for the training set of cardiac imaging data.

At 608, a deviation therebetween is stored as a user-specific calibration.

At 610, a coronary tree is segmented from CCTA imaging data of a patient under evaluation.

At 612, a user input indicative of an adjustment to the segmentation is received and applied to the segmented tree, producing a user adjusted coronary tree segmentation.

At 614, the user-specific calibration is applied to the user adjusted coronary vessel segmentation, producing an adapted user adjusted coronary tree segmentation for the patient.

At 616, an FFR index is generated using the adapted user adjusted coronary tree segmentation.

Figure 7:
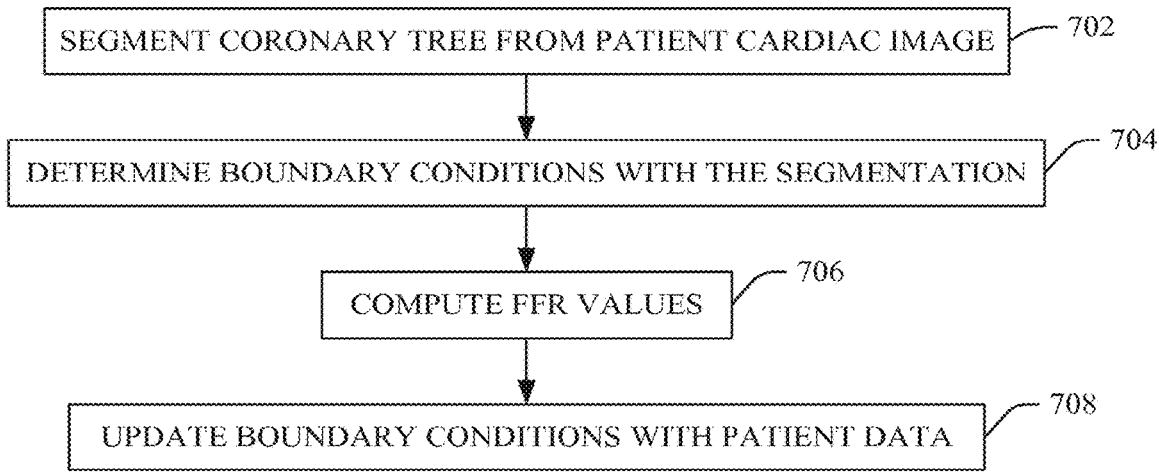
FIG. 7 illustrates another example method in accordance with an embodiment herein.

FIG. 7 illustrates another example method in accordance with an embodiment described herein.

At 702, a coronary tree is segmented from CCTA imaging data of a patient. In one instance, the coronary tree is adapted as described in connection with FIG. 6.

At 704, boundary conditions are determined based on the coronary tree.

At 706, FFR values are determined with the boundary conditions.

At 708, the boundary conditions are updated based on patient specific and/or other data.

The above may be implemented by way of computer readable instructions, encoded or embedded on computer readable storage medium, which, when executed by a computer processor(s), cause the processor(s) to carry out the described acts. Additionally, or alternatively, at least one of the computer readable instructions is carried by a signal, carrier wave or other transitory medium, which is not computer readable storage medium. Furthermore, it is to be appreciated that the ordering of the acts is not limiting. As such, other orderings are contemplated herein. In addition, one or more acts may be omitted and/or one or more additional acts may be included.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A computing system, comprising:
a computer readable storage medium with computer executable instructions, including a biophysical simulator with a segmentor and a boundary condition determiner; and
processor circuitry configured to execute the biophysical simulator to;
learn a deviation between a first user adjusted coronary tree segmentation and a reference coronary tree segmentation that results in a fractional flow reserve index that matches known ground truth invasive FFR measurements,
adapt a second user adjusted coronary tree segmentation from a non-training data set, based on the learned deviation between the first user adjusted coronary tree segmentation and the reference coronary tree segmentation, and
compute a fractional flow reserve index with cardiac imaging data and at least one of the adapted coronary tree segmentation and an adapted boundary condition.

2. The system of claim 1, wherein the cardiac imaging data includes training imaging, and segmentor generates the first user adjusted coronary tree segmentation from the cardiac imaging data with user interaction, and visually presents information indicative of the deviation between the first user adjusted coronary tree segmentation and the reference coronary tree segmentation.

3. The system of claim 1, wherein the cardiac imaging data includes training imaging, and segmentor generates the first user adjusted coronary tree segmentation from the cardiac imaging data with user interaction, and stores the deviation between the first user adjusted coronary tree segmentation and the reference coronary tree segmentation as calibration data.

4. The system of claim 3, wherein the segmentor subsequently processes cardiac imaging data of a patient, and generates the second user adjusted coronary tree segmentation from the cardiac imaging data with user interaction.

5. The system of claim 4, wherein the adaption includes shifting at least one point of the second user adjusted coronary tree segmentation, and wherein the shifting includes changing a diameter of a segmented coronary vessel.

6. The system of claim 4, wherein the segmentor visually presents the adapted segmentation for confirmation or rejection.

7. The system of claim 3, wherein the segmentor updates the calibration data based on a subsequent segmentation of the training imaging or other training imaging.

8. The system of claim 1, wherein the segmentor processes cardiac imaging data of a patient and generates the first user adjusted coronary tree segmentation from the cardiac imaging data with user interaction, and
wherein the boundary condition determiner determines boundary conditions based on the adapted segmentation or the first user adjusted coronary tree segmentation, and further comprising a flow simulator configured to compute the fractional flow reserve index based on the adapted segmentation or the first user adjusted coronary tree segmentation.

9. The system of claim 8, wherein the boundary condition determiner updates the boundary conditions based on patient-specific data.

10. The system of claim 9, wherein the boundary condition determiner determines a set of boundary conditions for a set of predetermined variations in the patient-specific data, and the flow simulator is configured to compute fractional flow reserve values based on the set of boundary conditions.

11. The system of claim 8, wherein the boundary condition determiner updates the boundary conditions based on documented outcomes, and the flow simulator is configured to compute fractional flow reserve values based on the set of boundary conditions.

12. The system of claim 8, wherein the patient-specific data includes a hematocrit, and the boundary condition determiner increases a viscosity of a blood boundary condition by scaling an initial value of the viscosity of blood boundary condition between a predetermined range in response to an elevated hematocrit.

13. The system of claim 8, wherein the patient-specific data indicates a presence of diabetes, and the boundary condition determiner increases a resistance boundary condition for a myocardium wall by adding a predetermined percentage to an initial value of the resistance boundary condition in response to the indication of the presence of diabetes.

14. The system of claim 8, wherein the patient-specific data indicates a presence of acute coronary syndrome, and the processor circuitry increases a cut-off fractional flow reserve threshold for treatment in response to the indication of the presence of acute coronary syndrome.

15. The system of claim 1, wherein the computed fractional flow reserve index matches known ground truth invasive fractional flow reserve measurements.

16. A non-transitory computer readable storage medium encoded with computer readable instructions which, when executed by processor circuitry cause the processor circuitry to perform a method comprising:
   receiving cardiac imaging data; and
   executing a biophysical simulator to;
   learn a deviation between a first user adjusted coronary tree segmentation and a reference coronary tree segmentation that results in a fractional flow reserve index that matches known ground truth invasive FFR measurements,
   adapt a second user adjusted coronary tree segmentation from a non-training data set, based on the learned deviation between the first user adjusted coronary tree segmentation and the reference coronary tree segmentation, and
   compute a fractional flow reserve index with the cardiac imaging data and at least one of the adapted coronary tree segmentation and an adapted boundary condition.

17. The non-transitory computer readable storage medium of claim 16, wherein the cardiac imaging data includes training imaging, and the processor circuitry generates the first user adjusted coronary tree segmentation from the cardiac imaging data with user interaction, and at least one of visually presents information indicative of the deviation between the first user adjusted coronary tree segmentation and the reference coronary tree segmentation or stores the deviation as calibration data.

18. The non-transitory computer readable storage medium of claim 17, wherein the cardiac imaging data includes imaging data for a patient under evaluation, and the processer circuitry generates the first user adjusted coronary tree segmentation from the imaging data with user interaction.

19. The non-transitory computer readable storage medium of claim 16, wherein the receive cardiac imaging data include cardiac imaging data of a patient, and the processor circuitry generates the first user adjusted coronary tree segmentation from the cardiac imaging data with user interaction, determines boundary conditions based on the adapted segmentation or the first user adjusted coronary tree segmentation, computes the fractional flow reserve index based on the boundary conditions, and updates the boundary conditions based on patient specific data collected after computing the fractional flow reserve index.

20. A method, comprising:
   receiving cardiac imaging data;
   learning a deviation between a first user adjusted coronary tree segmentation and a reference coronary tree segmentation that results in a fractional flow reserve index that matches known ground truth invasive FFR measurements;
   adapting a second user adjusted coronary tree segmentation from a non-training data set, based on the learned deviation between the first user adjusted coronary tree segmentation and the reference coronary tree segmentation; and
   computing a fractional flow reserve index with the cardiac imaging data and at least one of an adapted coronary tree segmentation and an adapted boundary condition.

21. The method of claim 20, wherein the cardiac imaging data includes training imaging, and further comprising:
   generating the first user adjusted coronary tree segmentation from the cardiac imaging data with user interaction;
   and
   at least one of visually presenting information indicative of the deviation between the first user adjusted coronary tree segmentation and the reference coronary tree segmentation or storing the deviation as calibration data.

22. The method of claim 21, wherein the cardiac imaging data includes imaging data for a patient under evaluation, and further comprising:
   generating the first user adjusted coronary tree segmentation from the imaging data with user interaction.

23. The method of claim 20, wherein the receive cardiac imaging data include cardiac imaging data of a patient, and further comprising:
   generating the first user adjusted coronary tree segmentation from the cardiac imaging data with user interaction;
   determining boundary conditions based on the adapted segmentation or the first user adjusted coronary tree segmentation;
   computing the fractional flow reserve index based on the boundary conditions; and
   updating the boundary conditions based on patient specific data collected after computing the fractional flow reserve index.

* * * * *